US010725034B2

(12) United States Patent
Duffy

(10) Patent No.: US 10,725,034 B2
(45) Date of Patent: Jul. 28, 2020

(54) ASSAYS FOR MACROMOLECULAR ANALYTES

(71) Applicant: Siemens Healthcare Diagnostics Inc., Tarrytown, NY (US)

(72) Inventor: James E. Duffy, Landenberg, PA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 18 days.

(21) Appl. No.: 16/289,776

(22) Filed: Mar. 1, 2019

(65) Prior Publication Data

US 2019/0195870 A1 Jun. 27, 2019

Related U.S. Application Data

(63) Continuation of application No. 15/030,086, filed as application No. PCT/US2014/061489 on Oct. 21, 2014, now abandoned.

(60) Provisional application No. 61/894,931, filed on Oct. 24, 2013.

(51) Int. Cl.
| | | |
|---|---|---|
| *G01N 33/53* | (2006.01) | |
| *G01N 33/543* | (2006.01) | |
| *G01N 33/566* | (2006.01) | |
| *G01N 33/545* | (2006.01) | |
| *G01N 33/68* | (2006.01) | |

(52) U.S. Cl.
CPC ..... *G01N 33/54393* (2013.01); *G01N 33/543* (2013.01); *G01N 33/545* (2013.01); *G01N 33/54306* (2013.01); *G01N 33/566* (2013.01); *G01N 33/6854* (2013.01)

(58) Field of Classification Search
None
See application file for complete search history.

(56) References Cited

U.S. PATENT DOCUMENTS

| | | | |
|---|---|---|---|
| 6,703,248 B1 * | 3/2004 | Singh | C12Q 1/6816 422/82.05 |
| 2005/0003459 A1 * | 1/2005 | Krutzik | B82Y 15/00 435/7.9 |
| 2008/0003626 A1 | 1/2008 | White et al. | |
| 2008/0268462 A1 | 10/2008 | Kosmeder et al. | |
| 2009/0258435 A1 | 10/2009 | Lewisch et al. | |
| 2010/0196878 A1 | 8/2010 | Vela Olmo et al. | |
| 2010/0285490 A1 | 11/2010 | Dees et al. | |
| 2011/0151582 A1 | 6/2011 | Basile | |

FOREIGN PATENT DOCUMENTS

| | | |
|---|---|---|
| EP | 0351248 A2 | 1/1990 |
| WO | 0127621 A2 | 4/2001 |

OTHER PUBLICATIONS

International Search Report and Written Opinion of International Application No. PCT/US2014/061489 dated Dec. 31, 2014.
European Supplementary Search Report and Written Opinion of European Application No. EP 14856561 dated Oct. 19, 2016.
European Notice of Allowance of European Application No. EP 14856561 dated Nov. 29, 2018.

* cited by examiner

*Primary Examiner* — Gary Counts

(57) ABSTRACT

A method of determining a macromolecular analyte in a sample suspected of containing the macromolecular analyte is disclosed. The sample and a conjugate reagent comprising a small molecule and a binding partner for the macromolecular analyte are combined in a medium. The conjugate reagent and a labeled binding partner for the small molecule are combined. The conjugate reagent or the medium is examined for an amount of labeled binding partner for the small molecule that is bound to the small molecule, which is related to the amount of the macromolecular analyte in the sample.

13 Claims, 2 Drawing Sheets

ASSAYS FOR MACROMOLECULAR ANALYTES

This is a continuation of application U.S. Ser. No. 15/030,086, filed Apr. 18, 2016, now abandoned which claims the benefit of US National Stage of International Application No. PCT/US2014/061489, filed Oct. 21, 2014 and claims priority under 35 U.S.C. 119(e) to U.S. Provisional Application No. 61/894,931, filed Oct. 24, 2013. All of the applications are incorporated by reference herein in their entirety.

BACKGROUND

The present invention relates generally to compositions and methods useful for determining the presence or absence of analytes, in particular, macromolecular analytes.

The clinical diagnostic field has seen a broad expansion over the years, both as to the variety of materials of interest that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

Diseases such as, for example, an infectious disease or autoimmune disease, manifest in the formation of an antibody against a specific antigen that is characteristic of the disease and is found in the blood of a patient. It is, therefore, important in the detection of such diseases to detect the presence and/or amount of the antibody against a specific antigen characteristic of such disease. Samples such as blood, e.g., serum, typically have a myriad of antibodies present in the sample. Methods are known for detection of antibodies against specific antigens. Such methods involve binding, either non-covalently or covalently, all of the antibodies in a sample with a reagent and then identifying, from all of the bound antibodies, the antibody against the specific antigen. As a result a large amount of this reagent must be used because a majority of the reagent binds to antibodies that are not directed to the specific antigen of interest. Examples of such approaches include contacting a human sample with a biotinylated mammalian anti-human IgG that recognizes and binds non-covalently to all human antibodies in the sample. In another example, all of the antibodies in a sample are biotinylated through the covalent binding of biotin to the antibodies.

There is a need for an assay for a macromolecular analyte such as an antibody that does not utilize a reagent that binds to all macromolecular substances in a sample. The assay should minimize the number of reagents necessary to measure the macromolecular analyte of interest that is present in a sample.

SUMMARY

One embodiment of the present invention is a method of determining a macromolecular analyte in a sample suspected of containing the macromolecular analyte. The sample and a reagent comprising a small molecule and a binding partner for the macromolecular analyte are combined in a medium. The reagent and a labeled binding partner for the small molecule are combined. The reagent or the medium is examined for an amount of labeled binding partner for the small molecule that is bound to the small molecule, which is related to the amount of the macromolecular analyte in the sample.

Another embodiment of the present invention is a method of determining an antibody analyte in a sample suspected of containing the antibody analyte. A combination is provided that comprises the sample, a support having bound thereto a small molecule and an antigen that binds to the antibody analyte, and a labeled binding partner for the small molecule. The medium is incubated under conditions for binding of the labeled binding partner to the small molecule. The support or the medium is examined for an amount of labeled binding partner for the small molecule that is bound to the small molecule and the amount thereof is related to the amount of the antibody analyte in the sample.

Another embodiment of the present invention is a method of determining an antibody analyte in a sample suspected of containing the antibody analyte. A combination is provided in a medium. The combination comprises the sample, a particle having bound thereto a small molecule and an antigen that binds to the antibody analyte, and a labeled binding partner for the small molecule. The medium is incubated under conditions for binding of the labeled binding partner to the small molecule. The support or the medium is examined for an amount of labeled binding partner for the small molecule that is bound to the small molecule and the amount thereof is related to the amount of the antibody analyte in the sample.

DETAILED DESCRIPTION OF SPECIFIC EMBODIMENTS

Figure 1:
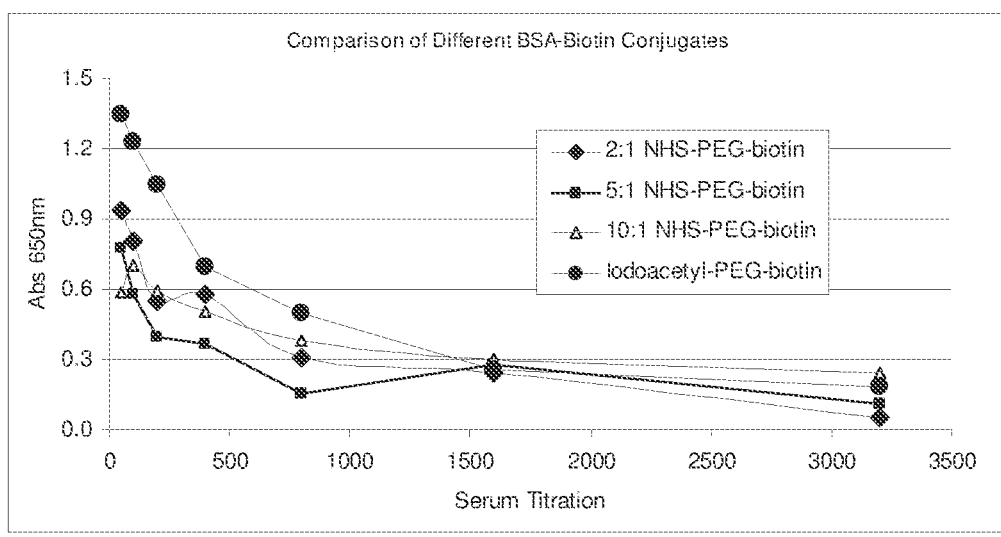
FIG. 1 is a graph showing a comparison of different biotinylated reagents used in carrying out a method in accordance with an example in accordance with the principles described herein.

Examples in accordance with the principles described herein provide a simple format for an assay for a macromolecular analyte such as, for example, a human antibody, which avoids the challenge of singling out the macromolecular analyte of interest from all the myriad macromolecular substances present in a patient sample. Examples in accordance with the principles described herein eliminate the need for non-covalent or covalent binding of a reagent to substantially all of the macromolecular substances present in a sample to be evaluated for a macromolecular analyte of interest. The use of such a reagent is avoided along with its associated cost and potential interference issues.

In examples in accordance with the principles described herein, a reagent system is employed wherein the reagents do not include a reagent that binds, either covalently or non-covalently, substantially all of the macromolecular substances present in a sample. Therefore, the reagent system is substantially free from a reagent that non-covalently or covalently binds to essentially all of the macromolecular substances in a sample. Examples in accordance with the principles described herein use a reagent system where the only interaction of a macromolecular analyte is with a specific binding partner for the macromolecular analyte. For example, for an antibody analyte, the only interaction of the antibody analyte is an antibody-antigen interaction where the target antibody of a sample recognizes a specific antigen employed in a reagent system in accordance with the principles described herein. In some examples, the specific antigen may be immobilized on a solid support. Through attraction of the sample antibody to the specific antigen, the antibody will physically block or sterically hinder the availability of a small molecule to a binding partner for the small molecule, which may be labeled or capable of being labeled (i.e., comprises a moiety that binds to a label such as, for example, a member of a specific binding pair). In some approaches in accordance with the principles described herein, a zero-level sample with no antibody will have high signal generation, and increasing amounts of antibody in the sample will progressively reduce the amount of signal generated from the label.

The term "analyte" refers to a component of interest; the compound or composition to be detected. The analyte is a member of a specific binding pair.

The term "macromolecular analyte(s)" refers to a substance that has a size or a shape or a combination of both size and shape that hinders the ability of a binding partner for a small molecule to bind to the small molecule when the small molecule is part of a reagent that also comprises a binding partner (for example, antigenic material) that is specific for the macromolecular substance. In some examples, macromolecular analytes are polymeric molecules that have a molecular weight (weight average molecular weight) of at least about 5,000, or at least about 10,000, or at least about 50,000, or at least about 100,000, or at least about 500,000, or at least about 1,000,000, for example. The molecular weight may be in a range of about 5,000 to about 10,000,000 or more, or 10,000 to about 10,000,000 or more, or about 10,000 to about 8,000,000, or about 10,000 to about 6,000,000, or about 10,000 to about 5,000,000 or about 10,000 to about 4,000,000, or about 10,000 to about 3,000,000 or about 10,000 to about 2,000,000, or about 10,000 to about 1,000,000, or about 50,000 to about 10,000,000 or more, or about 50,000 to about 8,000,000, or about 50,000 to about 6,000,000, or about 50,000 to about 5,000,000 or about 50,000 to about 4,000,000, or about 50,000 to about 3,000,000 or about 50,000 to about 2,000,000, or about 50,000 to about 1,000,000, or about 100,000 to about 10,000,000 or more, or about 100,000 to about 8,000,000, or about 100,000 to about 6,000,000, or about 100,000 to about 5,000,000 or about 100,000 to about 4,000,000, or about 100,000 to about 3,000,000 or about 100,000 to about 2,000,000, or about 100,000 to about 1,000,000, for example.

Macromolecular analytes may be, for example, poly (amino acids), i.e., polypeptides and proteins; carbohydrates, e.g., polysaccharides; or nucleic acids; and combinations thereof. Such combinations include, but are not limited to, components of bacteria, viruses, chromosomes, genes, mitochondria, nuclei, and cell membranes, for example. In the poly(amino acid) category, the poly(amino acids) of interest are from about 5,000 to 5,000,000 molecular weight, or from about 20,000 to 1,000,000 molecular weight; among hormones of interest, the molecular weights will usually range from about 5,000 to 60,000 molecular weight. In some examples, macromolecular analytes include, but are not limited to, antibodies, enzymes, hormones, polynucleotides, and carbohydrates.

A wide variety of proteins are included within the term poly(amino acids). Such proteins include, for example, immunoglobulins, cytokines, enzymes, hormones, cancer antigens, nutritional markers, tissue specific antigens, for example. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, α-fetoprotein, acid phosphatase, CA19.9 and CA125, tissue specific antigens, such as, e.g., alkaline phosphatase, myoglobin, CPK-MB and calcitonin, and peptide hormones. Other polymeric materials of interest are mucopolysaccharides and polysaccharides.

For immunoglobulin analytes, the molecular weights range from about 10,000 to about $2 \times 10^8$, or from about 10,000 to about $10^6$. For immunoglobulins, IgA, IgG, IgE and IgM, the molecular weights vary from about 160,000 to about $10^6$. Molecular weights of enzymes are in the range from about 10,000 to about 1,000,000. Natural receptors vary widely, generally being at least about 25,000 molecular weight and may be about $10^6$ or higher molecular weight, including such materials as avidin, DNA, RNA, thyroxine binding globulin, thyroxine binding prealbumin, and transcortin, for example. The term macromolecular analyte further includes polynucleotide analytes such as m-RNA, r-RNA, t-RNA, DNA, and DNA-RNA duplexes, for example.

The sample to be tested may be non-biological or biological. "Non-biological samples" are those that do not relate to a biological material and include, for example, soil samples, water samples, air samples, samples of other gases and mineral samples. The phrase "biological sample" refers to any biological material such as, for example, body fluid, body tissue, body compounds and culture media. The sample may be a solid, semi-solid or a fluid (a liquid or a gas) from any source. In some embodiments the sample may be a body excretion, a body aspirant, a body excisant or a body extractant. The body may be, for example, mammalian, reptilian, fish, plant, fungal, or bacterial. In some examples, the sample is that of a mammal and in some embodiments the body is a human body.

Body excretions are those substances that are excreted from a body (although they also may be obtained by excision or extraction) such as, for example, urine, feces, stool, vaginal mucus, semen, tears, breath, sweat, blister fluid and inflammatory exudates. Body excisants are those materials that are excised from a body such as, for example, skin, hair and tissue samples including biopsies from organs and other body parts. Body aspirants are those materials that are aspirated from a body such as, for example, mucus, saliva and sputum. Body extractants are those materials that are extracted from a body such as, for example, whole blood, plasma, serum, spinal fluid, cerebral spinal fluid, lymphatic fluid, synovial fluid and peritoneal fluid.

In some examples in accordance with the principles described herein, a reagent employed in the determination of a macromolecular analyte comprises a conjugate of a small molecule and a binding partner for the macromolecular analyte. In some examples in accordance with the principles described herein, a reagent employed in the determination of a macromolecular analyte comprises a support having bound thereto a small molecule and a binding partner for the macromolecular analyte, which may be bound individually to the support or may be bound as a conjugate of the small molecule and a binding partner for the macromolecular analyte.

The support may be solid or semi-solid and may be comprised of an organic or inorganic, water insoluble material, which may be transparent or partially transparent. The solid support can have any of a number of shapes such as, for example, particulate, including beads and particles, film, membrane, tube including hollow fiber, well, strip, rod, and planar surfaces such as, e.g., plate. Depending on the type of assay, the solid support may or may not be suspendable in the medium in which it is employed. Examples of a suspendable solid support include polymeric materials such as latex particles and magnetic particles. Other solid support compositions include polymers, such as poly (vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), for example; either used by themselves or in conjunction with other materials.

In some embodiments the support is a particle. The particles generally have an average diameter of about 0.02 to about 100 microns, or about 0.05 to about 100 microns, or about 0.1 to about 100 microns, or about 0.5 to about 100 microns, or about 0.02 to about 50 microns, or about 0.05 to about 50 microns, or about 0.1 to about 50 microns, or about 0.5 to about 50 microns, or about 0.02 to about 20 microns, or about 0.05 to about 20 microns, or about 0.1 to about 20 microns, or about 0.5 to about 20 microns, for example. In some embodiments, the particles have an average diameter from about 0.05 microns to about 20 microns or from about 0.3 microns to about 10 microns, or about 0.3 microns to about 5 microns, for example. In some embodiments, the particles are latex particles or magnetic particles, e.g., chrome particles.

In some examples in accordance with the principles described herein, the small molecule is an organic molecule that has a molecular weight less than about 2000, or less than about 1500, or less than about 1000, or less than about 500, or less than about 400, or less than about 300, for example. In some examples, the small molecule has a molecular weight in the range of about 100 to about 2,000, or about 100 to about 1,500, or about 100 to about 1,000, or about 100 to about 500, or about 100 to about 400, or about 100 to about 300, or about 100 to about 200, or about 200 to about 2,000, or about 200 to about 1,500, or about 200 to about 1,000, or about 200 to about 500, or about 200 to about 400, or about 200 to about 300, for example. Examples of small molecule-binding partner for the small molecule pairs, by way of illustration and not limitation, include biotin-binding partner for biotin (e.g., avidin, streptavidin, or antibody for biotin), desthiobiotin-binding partner for desthiobiotin (e.g., avidin, streptavidin, or antibody for desthiobiotin), digoxin-binding partner for digoxin (e.g., antibody for digoxin, etc.), fluorescein-binding partner for fluorescein (antibody for fluorescein, etc.), rhodamine-binding partner for rhodamine (e.g., antibody for rhodamine), and peptide-binding partner for the peptide (antibody for the peptide, etc.), for example.

The phrase "binding partner" refers to a molecule that is a member of a specific binding pair. A member of a specific binding pair is one of two different molecules having an area on the surface or in a cavity, which specifically binds to and is thereby defined as complementary with a particular spatial and polar organization of the other molecule. The members of the specific binding pair may be members of an immunological pair such as antigen-antibody or hapten-antibody, biotin-avidin, hormones-hormone receptors, enzyme-substrate, nucleic acid duplexes, IgG-protein A, and polynucleotide pairs such as DNA-DNA, DNA-RNA, for example.

The binding partner for the small molecule may be bound, either covalently or non-covalently, to a label to form a labeled binding partner for the small molecule or to a moiety to which the label may become bound. The label may be any molecule that is involved either directly or indirectly in the generation of a signal in the assay that corresponds to the presence of the analyte in a sample. The label is part of a signal producing system, which may have one or more components, at least one component being the label. The signal producing system generates a signal that relates to the presence of an analyte in a sample. The signal producing system includes all of the reagents required to produce a measurable signal. Other components of the signal producing system include, but are not limited to, substrates, enhancers, activators, chemiluminescent compounds, cofactors, inhibitors, scavengers, metal ions, specific binding substances required for binding of signal generating substances, for example. Other components of the signal producing system may be coenzymes, substances that react with enzymic products, other enzymes and catalysts, for example.

The label is capable of being detected directly or is detectable indirectly through, for example, a specific binding reaction that binds the label to a moiety that comprises a signal-generating component that produces a detectable signal. The label may be isotopic or non-isotopic, and can be, by way of illustration and not limitation, a polynucleotide coding for a catalyst, a promoter, a dye, a fluorescent molecule, a chemiluminescent molecule, a sensitizer including photosensitizers, an enzyme, a coenzyme, an enzyme substrate, a radioactive moiety, a small organic molecule, an amplifiable polynucleotide sequence, a support such as, for example, a particle such as, e.g., a latex or carbon particle, a metal sol, a crystallite, a liposome, a cell, a microtiter plate, for example. In some examples in accordance with the principles described herein, the label of the labeled binding partner is selected from the group consisting of enzymes, fluorescers, chemiluminescers, sensitizers, bioluminescers, electroluminescers, and radioactive moieties.

The support further comprises a binding partner for the macromolecular analyte, the nature of which is dependent upon the nature of the macromolecular analyte. For example, for a macromolecular analyte that is an antibody, the binding partner for the antibody may be an antigen that specifically binds to the antibody, i.e., a specific antigen for the antibody analyte. For a macromolecular analyte that is an enzyme, the binding partner for the enzyme may be a substrate for the enzyme. For a macromolecular analyte that is a polynucleotide, the binding partner for the polynucleotide may be a second polynucleotide that is complementary to the first polynucleotide.

The small molecule and the binding partner for the macromolecular analyte may each be associated individually with the support or the small molecule may be bound to the binding partner for the macromolecular analyte, which is associated with the support. The manner of association of the small molecule and/or the binding partner for the macromolecular analyte with a support depends on one or more of the nature of the support, the nature of the small molecule and the binding partner for the macromolecular analyte, the surface area and porosity of the support and the nature of any solvent employed, for example. The association may be by adsorption of the small molecule and/or the binding partner for the macromolecular analyte by the support, covalent bonding of the small molecule and/or the binding partner for the macromolecular analyte to the support, non-covalent bonding of the small molecule and/or the binding partner for the macromolecular analyte to the support by means of binding pair members (e.g., avidin-biotin and digoxin-antibody for digoxin), for example. In this manner the small molecule and/or the binding partner for the macromolecular analyte is "associated with" the solid support.

For binding of the small molecule to a binding partner for the macromolecular analyte to form a conjugate reagent or for the covalent binding of a small molecule and/or a binding partner for the macromolecular analyte to a support, a reactive functionality or functional group on one or more of the small molecule, the binding partner for the macromolecular analyte and the support may be employed to link the small molecule and/or the binding partner for the macromolecular analyte to one another and/or to the support. Functional groups on the small molecule and/or the binding partner for the macromolecular analyte may be present naturally or may be introduced synthetically and are discussed more fully below. The term "conjugate" refers to a compound formed by the covalent joining of two or more chemical compounds.

The nature of the functional groups employed is dependent on one or more of the nature of the support, the nature of the functional group on a small molecule and/or the binding partner for the macromolecular analyte, the nature of any coating such as, for example, a polysaccharide on the support, and flexibility in incorporation of functional groups on the support, for example. The functional groups may be naturally present or may be introduced synthetically by techniques that are well known in the art. The term "functional group" refers to a functionality that can react with a corresponding reactive functionality on another molecule to form a covalent bond. Such reactive functionalities include, by way of illustration and not limitation, aldehyde, carboxy, amino, imino, sulfhydryl and hydroxy, for example. A large number of suitable functional groups are available for attaching to amino groups (amine reactive functional groups), carboxy groups (carboxy reactive functional groups), sulfhydryls (sulfhydryl reactive functional groups), and alcohols (alcohol reactive functional groups), for example. Such functional groups include, but are not limited to, activated esters including, e.g., carboxylic esters, imidic esters, sulfonic esters and phosphate esters; activated nitrites; aldehydes; ketones; maleimides; haloalkylamides; and alkylating agents, for example.

In some examples functional groups are present on the support and/or on the small molecule and/or the binding partner for the macromolecular analyte by means of a linking group, which may comprise a chain of from 1 to about 60 or more atoms, or 1 to about 50 atoms, or 1 to about 40 atoms, or 1 to 30 atoms, or about 1 to about 20 atoms, or about 1 to about 10 atoms, or about 5 to about 60 or more atoms, or about 5 to about 50 atoms, or about 5 to about 40 atoms, or about 5 to 30 atoms, or about 5 to about 20 atoms, or about 5 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, or about 2 to about 4, and include heteroatoms that may be present in a functional group on the linking group. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their particular function such as, for example, their function in an assay. The linking group may be aliphatic or aromatic. When heteroatoms are present, oxygen will normally be present as oxy or oxo, bonded to carbon, sulfur, nitrogen or phosphorous; sulfur will be present as thioether or thiono; nitrogen will normally be present as nitro, nitroso or amino, normally bonded to carbon, oxygen, sulfur or phosphorous; phosphorous will be bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth. The linking group may also be a macro-molecule such as polyethers, polysaccharides, peptides, proteins, nucleotides, and dendrimers.

As mentioned above, a small molecule may be bound to the binding partner for the macromolecular analyte to form a conjugate rather than being bound directly to the support. The small molecule and the binding partner for the macromolecular analyte may each contain a functionality that is reactive with one another. Such functionalities include those mentioned above for binding the small molecule and/or the binding partner for the macromolecular analyte to a support.

In the method of determining a macromolecular analyte in a sample suspected of containing the macromolecular analyte, the sample and a conjugate reagent comprising a small molecule and a binding partner for the macromolecular analyte, which may or may not be bound to a support, are combined in a medium, which may be an assay medium. In some examples, the assay medium is an aqueous buffered medium having a moderate pH. The aqueous medium may be solely water or may include from 0.1 to about 40 volume percent of a cosolvent such as, for example, a water miscible organic solvent, e.g., an alcohol, an ether or an amide. The pH for the medium will usually be in the range of about 4 to about 11, or in the range of about 5 to about 10, or in the range of about 6.5 to about 9.5, for example. The pH utilized is often the result of a compromise between optimum binding of the binding members of any specific binding pairs and the pH optimum for other reagents of the assay such as members of the signal producing system, for example. Various buffers may be used to achieve the desired pH and maintain the pH during the determination. Illustrative buffers include, by way of illustration and not limitation, borate, phosphate, carbonate, Tris (tris(hydroxymethyl)-aminomethane), barbital, PIPES, HEPES, IVIES, ACES, MOPS, and BICINE, for example. The particular buffer employed is not critical, but in an individual assay one or another buffer may be preferred.

Various ancillary materials may be employed in the assay medium. For example, in addition to buffers the medium may comprise one or more of stabilizers for the medium and for the reagents employed and salts to increase the ionic strength, for example. In some examples, in addition to these additives, the medium may include proteins such as, e.g., albumins; organic solvents such as, e.g., formamide; quaternary ammonium salts; polyanions such as, e.g., dextran sulfate; binding enhancers, e.g., polyalkylene glycols; polysaccharides such as, e.g., dextran, trehalose, or the like. The medium may also comprise agents for preventing the formation of blood clots. Such agents are well known in the art and include, for example, EDTA, EGTA, citrate and heparin. The medium may also comprise one or more preservatives as are known in the art such as, for example, sodium azide, neomycin sulfate, PROCLIN® 300 and Streptomycin. Any of the above materials, if employed, is present in a concentration or amount sufficient to achieve the desired effect or function.

The conjugate reagent and the labeled binding partner for the small molecule are combined. In some examples, the sample, the conjugate reagent and the labeled binding partner for the small molecule are combined sequentially and, in some examples, the sample, the conjugate reagent and the labeled binding partner are combined substantially simultaneously. In some examples, the simplest order of addition is to add all the materials simultaneously and examine the medium or the conjugate reagent for an amount of signal as in a homogeneous assay. Alternatively, as mentioned above, the reagents can be combined sequentially.

When the above reagents are combined sequentially, one or more incubation periods may be employed between the combining steps. Thus, one or more incubation periods may be applied to the medium at one or more intervals including any intervals between additions of various reagents for determining the macromolecular analyte. The nature of the incubation periods (e.g., duration and temperature) is dependent on the nature of a particular assay method employed in the present determinations. In many embodiments, the medium is incubated at a temperature and for a time sufficient for binding of binding partners to occur and for the binding and reaction of various other reagents to occur. Moderate temperatures are normally employed for carrying out the method. Incubation temperatures may range from about 5° C. to about 70° C., or from about 15° C. to about 70° C., or from about 20° C. to about 45° C., for example. The time period for an incubation is about 0.2 seconds to about 6 hours, or about 2 seconds to about 1 hour, or about 1 to about 5 minutes, for example. The time period depends on the temperature of the medium and the rate of binding of the various reagents, which is determined by the association rate constant, the concentration, the binding constant and dissociation rate constant.

Following the combination of the conjugate reagent and the labeled binding partner for the small molecule, the conjugate reagent or the medium is examined for an amount of labeled binding partner bound to the small molecule. In some examples, the reagent or the medium is examined for an amount of signal from the label of the labeled binding partner for the small molecule. Where the medium is examined for an amount of signal from the label, a known, controlled quantity of the labeled binding partner for the small molecule may be employed, which is in excess of the maximum amount of macromolecular analyte expected to be present in a sample. In either approach, measuring the amount of signal from the label allows measuring an amount of macromolecular analyte in the sample.

The phrase "measuring the amount of macromolecular analyte" refers to the quantitative, semiquantitative and qualitative determination of the macromolecular analyte. Methods that are quantitative, semiquantitative and qualitative, as well as all other methods for determining the macromolecular analyte, are considered to be methods of measuring the amount of the macromolecular analyte. For example, a method, which merely detects the presence or absence of the macromolecular analyte in a sample suspected of containing the macromolecular analyte, is considered to be included within the scope of the present invention. The terms "detecting" and "determining," as well as other common synonyms for measuring, are contemplated within the scope of the present invention. The phrase "sample suspected of containing the analyte" includes determining whether or not an analyte is present in a sample. Thus, the phrase applies to both determining the presence or absence of analyte in the sample. Included within the scope of the phrase is analyzing a sample that is not suspected of containing the analyte.

As mentioned above, the examination of the conjugate reagent or the medium involves detection of a signal from the conjugate reagent or the medium. The presence and/or amount of the signal are related to the presence and/or amount of the macromolecular analyte in the sample. The particular mode of detection depends on one or more of the nature of the particular assay system employed and the nature of the signal producing system member(s) employed including the label. As discussed above, there are numerous methods by which a label can be employed to result in the generation of a signal, which in some embodiments is detectable by external means.

Activation of a signal producing system depends on the nature of the signal producing system members. Luminescence or light produced as a result of activation of the signal producing system can be measured visually, photographically, actinometrically, spectrophotometrically or by any other convenient means to determine the amount thereof, which is related to the amount of macromolecular analyte in the medium. The examination for presence and/or amount of the signal also includes the detection of the signal, which is generally merely a step in which the signal is read. The signal is normally read using an instrument, the nature of which depends on the nature of the signal. The instrument may be a spectrophotometer, fluorometer, absorption spectrometer, luminometer, chemiluminometer, and the like.

Temperatures during measurements generally range from about 10° C. to about 70° C. or from about 20° C. to about 45° C., or about 20° C. to about 25° C. In some embodiments the temperature during measurement is substantially constant. In one approach standard curves are formed using known concentrations of the analyte. Calibrators and other controls may also be used.

The concentration of macromolecular analyte that may be assayed generally varies from about $10^{-5}$ to about $10^{-17}$ M, more usually from about $10^{-6}$ to about $10^{-14}$ M. Considerations, such as whether the assay is qualitative, semiquantitative or quantitative (relative to the amount of macromolecular analyte present in the sample), the particular detection technique and the concentration of the macromolecular analyte normally determine the concentrations of the various reagents. The concentration range of interest of the macromolecular analyte will generally determine the concentrations of the various reagents in the assay medium. However, the final concentration of each of the reagents is normally determined empirically to optimize the sensitivity of the assay over the range. That is, a variation in concentration of macromolecular analyte that is of significance should provide an accurately measurable signal difference. Considerations such as the nature of the signal producing system and the nature of the analytes normally determine the concentrations of the various reagents.

General Description of Assays in which the Antibodies May be Utilized

The following discussion is by way of illustration and not limitation. Approaches in accordance with the principles described herein may be employed in any assay format that permits a method that is in accordance with the principles described herein. The assay format should allow for binding of a binding partner for a macromolecular analyte to the macromolecular analyte where the binding blocks or sterically hinders the binding between a small molecule associated with the binding partner for the macromolecular analyte and a binding partner for the small molecule.

The assays can be performed either without separation (homogeneous) or with separation (heterogeneous) of any of the assay components or products and may be manual or automated. Heterogeneous assays usually involve one or more separation steps and can be competitive or non-competitive. The assays involve the binding between members of a specific binding pair. The specific binding pair members in many instances are members of an immunological pair such as antigen-antibody and the assays are referred to as immunoassays. As discussed above, other specific binding pairs such as, for example, biotin-avidin, hormones-hormone receptors, enzyme-substrate, nucleic acid duplexes, IgG-protein A, and polynucleotide pairs such as DNA-DNA, DNA-RNA, are not immunological pairs but are included within the scope of sbp member. Assay methods similar to immunoassay techniques are applicable to members of specific binding pairs other than antigen-antibody specific binding pairs.

In many embodiments immunoassays involve labeled reagents. Immunoassays that involve labeled reagents include, but are not limited to, chemiluminescence immunoassays, enzyme immunoassays, fluorescence polarization immunoassays, radioimmunoassays, inhibition assay, induced luminescence assays, and fluorescent oxygen channeling assays, for example. Included within the scope of assays that may be employed are immunoassays using a limited concentration of one of the assay reagents and immunoassays that use of an excess of one or more of the principal reagents.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; the induced luminescence immunoassay ("LOCI® technology") disclosed in U.S. Pat. No. 5,340,716 (Ullman, et al.); immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The above disclosures are all incorporated herein by reference.

Other enzyme immunoassays are the enzyme modulator mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), and particle enhanced turbidimetric immunoassay ("PETIA"), etc.; for example.

Other assays include the sol particle immunoassay ("SPIA"), the disperse dye immunoassay ("DIA"); the metalloimmunoassay ("MIA"); the enzyme membrane immunoassays ("EMIA"); luminoimmunoassays ("LIA"); and so forth. Other types of assays include immunosensor assays involving the monitoring of the changes in the optical, acoustic and electrical properties of a reagent upon the binding of an analyte. Such assays include, for example, optical immunosensor assays, acoustic immunosensor assays, semiconductor immunosensor assays, electrochemical transducer immunosensor assays, potentiometric immunosensor assays, and amperometric electrode assays.

In an example of a homogeneous assay, by way of example and not limitation, a conjugate reagent comprising a small molecule and a binding partner for a macromolecular analyte are combined with a medium containing the sample suspected of containing the macromolecular analyte where a labeled binding partner for the small molecule is also included. If macromolecular analyte is present, the macromolecular analyte binds to the binding partner for the macromolecular thereby sterically hindering and blocking the binding of the labeled binding partner for the small molecule to the small molecule of the conjugate reagent. In this example, a decrease in signal from the label is realized. The signal may be determined by conventional techniques and a reduction in the amount of signal is related to the amount of the macromolecular analyte in the sample. Depending on the nature of a particular assay format employed, an increase in signal may be observed.

Many known assays utilize a signal producing system that employs first and second signal producing system members. The signal producing system members may be related in that activation of one member of the signal producing system produces a product such as, e.g., light, which results in activation of another member of the signal producing system.

In a homogeneous variation of the above assay, a sample suspected of containing a macromolecular analyte in a suitable medium is contacted with a support having bound thereto a small molecule and a binding partner for the macromolecular analyte; the support comprises a label. Optionally, the medium is incubated for a period of time. The support is contacted with a labeled binding partner for the small molecule that comprises a second label where a product of the activation of one of the labels is reactive with the other of the labels. After an incubation period, the support is examined for the presence of a signal, which is related to the presence or amount of analyte.

In a heterogeneous variation of the above assay, a sample suspected of containing a macromolecular analyte in a suitable medium is contacted with a support having bound thereto a small molecule and a binding partner for the macromolecular analyte. The medium is incubated for a period of time. The support is separated from the medium and washed to remove unbound materials. The support is contacted with a labeled binding partner for the small molecule. After an incubation period, the support is examined for the presence of a signal from the label, which is related to the presence or amount of analyte.

In some embodiments of known assays, the members of the signal producing system comprise a sensitizer such as, for example, a photosensitizer, and a chemiluminescent composition where activation of the sensitizer results in a product that activates the chemiluminescent composition. One signal producing system member generates a detectable signal that relates to the amount of bound and/or unbound signal producing system member, i.e. the amount of signal producing system member bound or not bound to the conjugate reagent or to an agent that reflects the amount of the macromolecular analyte to be detected. In some examples in accordance with the principles described herein, the label employed, for example, in labeled binding partner for the small molecule, may be one of either the sensitizer reagent or the chemiluminescent reagent or may be an specific binding pair member that binds to a complementary specific binding pair member that comprises either the sensitizer or the chemiluminescent reagent. The other of the labels, e.g., sensitizer or chemiluminescent reagent, may be bound to the conjugate reagent comprising the small molecule and the binding partner for the macromolecular analyte. An embodiment of such an assay is the induced luminescence immunoassay (LOCI® assay). As indicated above, the induced luminescence immunoassay is described in U.S. Pat. No. 5,340,716 (Ullman), which disclosure is incorporated herein by reference.

A chemiluminescent compound (chemiluminescer) is a compound that is chemically activatable and, as a result of such activation, emits light at a certain wavelength. Examples of chemiluminescers, by way of illustration and not limitation, include olefins capable of reacting with singlet oxygen or a peroxide to form hydroperoxides or dioxetanes, which can decompose to ketones or carboxylic acid derivatives; stable dioxetanes which can decompose by the action of light; acetylenes which can react with singlet oxygen to form diketones; hydrazones or hydrazides that can form azo compounds or azo carbonyls such as luminol; and aromatic compounds that can form endoperoxides, for example. As a consequence of the activation reaction, the chemiluminescers directly or indirectly cause the emission of light.

A sensitizer is a molecule, usually a compound, for generation of a reactive intermediate such as, for example, singlet oxygen, for activation of a chemiluminescent compound. In some embodiments, the sensitizer is a photosensitizer. Other sensitizers that can be chemi-activated (by, e.g., enzymes and metal salts) include, by way of example and not limitation, other substances and compositions that can produce singlet oxygen with or, less preferably, without activation by an external light source. For example, certain compounds have been shown to catalyze the conversion of hydrogen peroxide to singlet oxygen and water. Also included within the scope of photosensitizers are compounds that are not true sensitizers but which on excitation by heat, light, ionizing radiation, or chemical activation will release a molecule of singlet oxygen. Members of this class of compounds include, for example, the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

A photosensitizer is a sensitizer for activation of a photoactive compound, for example, by generation of singlet oxygen by excitation with light. The photosensitizers are photoactivatable and include, e.g., dyes and aromatic compounds, and are usually compounds comprised of covalently bonded atoms, usually with multiple conjugated double or triple bonds. The compounds should absorb light in the wavelength range of 200 to 1,100 nm, or 300 to 1,000 nm, or 450 to 950 nm, with an extinction coefficient at its absorbance maximum greater than 500 $M^{-1}$ $cm^{-1}$, or greater than 5,000 $M^{-1}$ $cm^{-1}$, or greater than 50,000 $M^{-1}$ $cm^{-1}$, at the excitation wavelength. Photosensitizers should be relatively photostable and, preferably, not react efficiently with singlet oxygen. Examples of photosensitizers, by way of illustration and not limitation, include acetone, benzophenone, 9-thioxanthone, eosin, 9,10-dibromoanthracene, methylene blue, metallo-porphyrins, such as hematoporphyrin, phthalocyanines, chlorophylls, rose bengal, and buckminsterfullerene, for example, and derivatives of these compounds.

Examples of chemiluminescent compounds and photosensitizers that may be utilized in embodiments of assays employing methods in accordance with the principles described herein are set forth in U.S. Pat. No. 5,340,716 (Ullman, et al.), the relevant portions of which disclosure are incorporated herein by reference.

In one example of an induced luminescence immunoassay by way of example and not limitation, the assay uses a particle associated with a chemiluminescent reagent where the particle has a small molecule (e.g., biotin) and a binding partner for the macromolecular analyte bound to the particle. A second particle is employed that is labeled with a photosensitizer and has a binding partner for the small molecule bound thereto such as, for example, a binding partner for biotin such as, e.g., avidin or streptavidin (photosensitizer reagent). The chemiluminescent reagent comprising the small molecule and the binding partner for the macromolecular analyte binds to macromolecular analyte and, as a result, the binding of the binding partner for the small molecule of the photosensitizer reagent to the small molecule of the chemiluminescent reagent is blocked, thereby reducing the amount of the photosensitizer reagent the becomes bound to the chemiluminescent reagent. Thus, the more macromolecular analyte in the sample, the greater is the reduction in the signal produced by the photosensitizer and the chemiluminescent compound coming into close proximity by virtue of binding of the binding partner for the small molecule with the small molecule of the chemiluminescent reagent. The photosensitizer generates singlet oxygen and activates the chemiluminescent reagent when the two labels are in close proximity. The activated chemiluminescent reagent subsequently produces light. The amount of light produced is inversely related to the amount of the complex formed between the photosensitizer reagent and the chemiluminescent reagent, which in turn is related to the amount of macromolecular analyte present in a sample.

In some examples of an induced luminescence assay by way of illustration and not limitation, a photosensitizer particle is employed that is conjugated to avidin or streptavidin. A biotinylated binding partner for the macromolecular analyte is employed as part of a particle reagent that is labeled with a chemiluminescent reagent. The reaction medium is incubated to allow the binding partner for the macromolecular analyte to bind to the macromolecular analyte and to allow the photosensitizer particles to bind to the biotinylated macromolecular analyte by virtue of the binding between avidin and biotin. Then, the medium is irradiated with light to excite the photosensitizer, which is capable in its excited state of activating oxygen to a singlet state. Because the chemiluminescent reagent is now in close proximity to the photosensitizer by virtue of the presence of the analyte, it is activated by the singlet oxygen and emits luminescence. The medium is then examined for the presence and/or the amount of luminescence or light emitted, the presence thereof being related to the presence and/or amount of the analyte. Because the presence of macromolecular analyte in the sample results in blocking of the binding between the small molecule of the chemiluminescent reagent and the binding partner for the small molecule that is part of the photosensitizer reagent, a decrease in the amount of signal produced is observed in the presence of macromolecular analyte and is related to the amount of macromolecular analyte in the sample.

Another example, by way of illustration and not limitation, of an assay format for detection of a macromolecular analyte is an assay format utilizing a magnetic particle such as, for example, a chrome particle. For this assay format, chrome particles, to which are bound a small molecule and a binding partner for the macromolecular analyte, are employed. A reagent comprising a labeled binding partner for the small molecule is also employed where the label is, by way of illustration and not limitation, an enzyme such as, for example, an acridinium ester. The magnetic particle reagent is combined with a sample suspected of containing the macromolecular analyte, which, if present, binds to the binding partner for the macromolecular analyte of the magnetic particle reagent. The reagent comprising the labeled binding partner for the small molecule is added and the medium is incubated. Then, a magnet is applied, which pulls all of the magnetic particles out of the suspension, and either the magnetic particles or the supernatant is transferred to a final reaction container. The magnetic particles or the supernatant is examined for the amount of signal from the label, which is then related to the amount of macromolecular analyte in the sample. In one example where the label is an enzyme, a substrate for the enzyme is added, and enzyme activity is measured spectrophotometrically as a change in absorbance over time. The amount of this signal is related to the amount of macromolecular analyte in the sample. Where the magnetic particles are examined for the amount of signal, the amount of signal is inversely proportional to the amount of macromolecular analyte in the sample. Where the supernatant is examined for the amount of signal, the amount of signal is directly proportional to the amount of macromolecular analyte in the sample.

As mentioned above, the sample and reagents are provided in combination in the medium. While the order of addition of reagents to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

Kits Comprising Reagents for Conducting Assays

Reagents for carrying out an assay for a macromolecular analyte in accordance with the principles described herein and other reagents for conducting a particular assay for a macromolecular analyte may be present in a kit useful for conveniently performing an assay for the determination of a macromolecular analyte. In some examples a kit comprises in packaged combination a conjugate reagent comprising a small molecule and a binding partner for the macromolecular analyte. The conjugate reagent may be a liquid phase or a solid phase reagent where the conjugate reagent also comprises a support. The kit may also comprise a labeled binding partner for the small molecule and may also include members of a signal producing system other than the label. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members and ancillary reagents, for example.

The relative amounts of the various reagents in the kits can be varied widely to provide for concentrations of the reagents that substantially optimize the reactions that need to occur during the assay methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay utilizing embodiments of the present conjugates. The kit can further include a written description of a method as described above.

Definitions

The following definitions as used in this specification and the appended claims are provided for terms and phrases not otherwise specifically defined above. It is to be understood that the terminology used herein is for the purpose of describing particular embodiments only and is not intended to be limiting.

The phrase "at least" as used herein means that the number of specified items may be equal to or greater than the number recited.

The phrase "about" as used herein means that the designated value may vary by plus or minus twelve percent, or eleven percent, or ten percent, or nine percent, or eight percent, or seven percent, or six percent, or five percent, or four percent, or three percent, or two percent, or one percent. For example, "about 5" with a variance of plus or minus 10% means a range of 4.5 to 5.5.

The designations "first" and "second" are used solely for the purpose of differentiating between two items such as, for example, "first label" and "second label," or "first sbp member" and "second sbp member" and are not meant to imply any sequence or order or importance to one item over another or any order of addition, for example.

The singular forms "a", "an" and "the" include plural referents unless the content clearly dictates otherwise.

The term "substantially" when not specifically defined above varies with the context as understood by those skilled in the relevant art and generally means at least 70%, or at least 80%, or least 90%, or at least 95%, or at least 99%, or 100%.

"Optionally" means that the specified item may be present or may not be present.

The following examples further describe specific embodiments of the invention by way of illustration and not limitation and are intended to describe and not to limit the scope of the invention. Parts and percentages disclosed herein are by volume unless otherwise indicated.

Examples

In the following example, an ELISA assay format was employed to quantitate anti-BSA antibodies in an immunized mouse serum sample, i.e., serum from mice that were previously inoculated with a BSA-based immunogen. Biotinylated BSA was produced and immobilized onto an ELISA plate to serve as a capture phase for the anti-BSA antibodies of the sample, with subsequent signal generation provided by a commercially-available streptavidin-HRP conjugate.

Materials:

Unless indicated otherwise, reagents were purchased from Sigma-Aldrich (Milwaukee, Wis.) and used as received.

Abbreviations:
 BSA—bovine serum albumin
 HRP—horse radish peroxidase
 NHS—N-hydroxysuccinimide
 PEG—polyethylene glycol
 hrs—hours
 min—minutes
 mL—milliliters
 mg—milligrams
 g—grams
 mM—millimolar
 kDa—kilodalton(s)
 nm—nanometer(s)
 vol—volume
 wt—weight Preparation of Reagents To form the biotinylated antigenic material, bovine serum albumin was derivatized with biotinylation reagents through primary amines and thiol groups. For the amine-derivatized material, 60 mg bovine serum albumin (Millipore Corp., Kankakee Ill.) was dissolved at a concentration of 10 mg/mL in 10 mM sodium phosphate pH 7.0/300 mM NaCl, and then divided into 3×20 mg aliquots. To each respective aliquot was added NHS-PEG$_4$-biotin (Thermo Scientific, Rockford Ill.) sufficient for 2:1, 5:1, and 10:1 molar challenge ratios of biotin to protein. The mixtures were allowed to react at room temperature for 3 hrs, and then the mixtures were purified into the same pH 7 buffer over a 1.6×28 cm SEPHADEX® G-25 (GE Healthcare Bio-Sciences, Uppsala, Sweden) column. Protein concentration of the product was determined by absorbance at A280 nm.

For the thiol-derivatized material, BSA was dissolved at 10 mg/mL in 100 mM sodium phosphate pH 8.0. Iodoacetyl-PEG$_2$-biotin (Thermo Scientific, Rockford Ill.) was added in an amount sufficient for a 20:1 molar challenge ratio of biotin to protein. The mixture was allowed to react at room temperature overnight, then the mixture was fractionated over a 21.2×300 mm BIOSEP® SEC-53000 column (Phenomenex, Torrance Calif.) into 10 mM sodium phosphate pH 7.0/300 mM NaCl; the monomer 66 kDa fractions were pooled. Protein concentration of the product was determined by absorbance at A280 nm.

Assay

Flat-bottom polystyrene ELISA plates, 96-well (Thermo Fisher Nunc, Rochester, N.Y.) were coated separately with the various biotinylated BSA preparations from above diluted to 1 μg/mL target concentrations. The plates were washed with a wash solution, which was deionized water containing 0.05% vol/vol TWEEN® 20 (Sigma-Aldrich, St. Louis, Mo.), blocked with BioWhittaker Dulbecco's Phosphate-Buffered Saline (Lonza, Walkersville, Md.) with added 0.5% wt/vol casein (MP Biomedicals, LLC, Solon, Ohio) and 0.05% vol/vol TWEEN® 20 (Sigma-Aldrich, St. Louis, Mo.), and then washed again with the wash solution. Dilutions of mouse serum sample, immunized versus a non-immunized serum control, were then added followed by another wash step as above. Streptavidin-HRP conjugate (ZyMed, San Francisco Calif.) was added at a 1:1000 dilution, followed by a last wash step with the above wash solution. TMB substrate (Moss Substrates, Inc., Pasadena Md.) was added, and the signal generated was measured by A650 nm.

FIG. 1 indicates the results for each of the four biotinylated BSA materials produced, expressed as the A650 of the non-immunized serum response subtracted from that of the immunized response versus serum dilution. A decreasing difference with respect to sample dilution results from increasing signal generation due to reduced amounts of anti-BSA sample antibodies physically blocking the binding of biotin of the biotinylated BSA with the streptavidin of the streptavidin-HRP conjugate.

Figure 2:
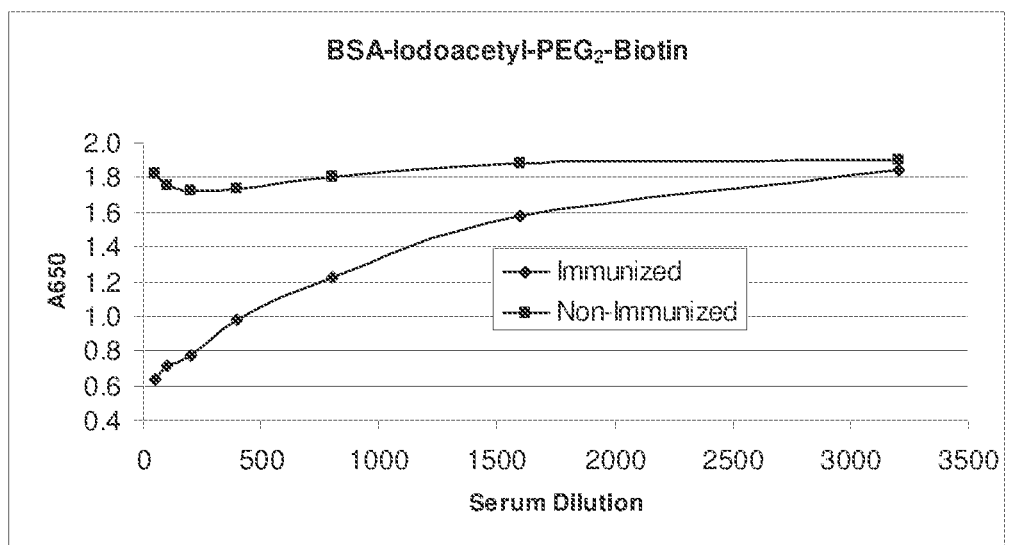
FIG. 2 is a graph showing a plot for one of the biotinylated reagents of FIG. 1 used in carrying out a method in accordance with an example in accordance with the principles described herein.

FIG. 2 is a re-plot of the data for the best-performing material from above, the BSA-iodoacetyl-PEG$_2$-biotin (thiol-derivatized), expressed as A650 versus serum dilution for both immunized and non-immunized serum. The non-immunized sample is shown to give a steadily high signal regardless of dilution, as there is no anti-BSA antibody present in the sample to block the binding of the streptavidin-HRP conjugate to the immobilized biotinylated BSA. In contrast, the immunized sample shows a low signal from a low dilution of sample due to the blocking effect of the anti-BSA antibodies present in the sample, with steadily rising signal with increasing dilution due to decreasing amounts of blocking of binding of the biotin of the biotinylated BSA with the streptavidin of the streptavidin-HRP conjugate.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of determining a macromolecular analyte in a sample suspected of containing the macromolecular analyte, the method comprising:
   (a) combining in a medium the sample and a conjugate reagent comprising a small molecule and a binding partner for the macromolecular analyte,
   (b) combining the mixture from step (a) and a labeled binding partner for the small molecule, and
   (c) examining the conjugate reagent or the medium for an amount of labeled binding partner for the small molecule that is bound to the small molecule and relating the amount thereof to the amount of the macromolecular analyte in the sample,
   wherein said macromolecular analyte binds to the binding partner for the macromolecular analyte of the conjugate reagent and such macromolecular analyte has a size or a shape or a combination of both size and shape that blocks the ability of the binding partner for the small molecule to bind to the small molecule of the conjugate reagent, wherein the macromolecular analyte has a molecular weight of at least 5000 and is selected from the group consisting of antibodies, enzymes, hormones, polynucleotides, and carbohydrates, and wherein the small molecule is an organic molecule that has a molecular weight in the range of from 100 to 2000, comprises functional groups that are reactive with the binding partner for the macromolecular analyte and is bound to the binding partner for the macromolecular analyte.

2. The method according to claim 1, wherein the macromolecular analyte is an antibody analyte, the labeled binding partner for the macromolecular analyte is an antigen that binds to the antibody analyte, and the small molecule and the antigen that binds to the antibody analyte are bound to a support, the method further comprising:

incubating the medium under conditions for binding of the labeled binding partner to the small molecule, and examining the support or the medium for an amount of labeled binding partner bound to the small molecule and relating the amount thereof to the amount of the antibody analyte in the sample.

3. The method according to claim 1, wherein the small molecule and the labeled binding partner for the macromolecular analyte are bound to a particle, the method further comprising:

incubating the medium under conditions for binding of the labeled binding partner to the small molecule, and examining the support or the medium for an amount of labeled binding partner bound to the small molecule and relating the amount thereof to the amount of the macromolecular analyte in the sample.

4. The method according to claim 1 wherein the conjugate reagent further comprises a support to which the small molecule and the binding partner for the macromolecular analyte are bound.

5. The method according to claim 4 or 2, wherein the support is a non-magnetic particle, a magnetic particle, a plate, or a tube.

6. The method according to claim 1 or 2, wherein the small molecule is selected from the group consisting of biotin, desthiobiotin, dinitrophenol, digoxin, digoxigenin, rhodamine, and fluorescein.

7. The method according to claim 2, wherein the label of the labeled binding partner is selected from the group consisting of enzymes, fluorescers, chemiluminescers, bioluminescers, electroluminescers, sensitizers, and radioactive materials.

8. The method according to claim 4 or 2, wherein the support comprises a label wherein the label is interactive with the label of the labeled binding partner.

9. The method according to claim 1 or 2, wherein the sample is a body excretion, body aspirant, body excisant or body extractant.

10. The method according to claim 1 or 2, wherein the method is a homogeneous assay method.

11. The method according to claim 3, wherein the labeled binding partner is labeled with a particle comprising a sensitizer label and the particle having bound thereto a small molecule comprises a chemiluminescent label.

12. The method according to claim 3, wherein the particle having bound thereto a small molecule is a magnetic particle.

13. The method according to claim 3, wherein the small molecule is bound to the labeled binding partner, which is bound to the particle.

* * * * *